(12) United States Patent
Ruckmick et al.

(10) Patent No.: US 7,534,795 B2
(45) Date of Patent: May 19, 2009

(54) COMPOUNDS AND THEIR USE RELATED TO COMPOSITIONS FOR TREATING DISEASE

(75) Inventors: Stephen Ruckmick, Laguna Niguel, CA (US); Robert Cain, Irvine, CA (US); Milton J. Abreo, Lake Forest, CA (US); Massoud Fahid, Fullerton, CA (US); Brent A. Johnson, Ladera Ranch, CA (US)

(73) Assignee: Allergan, Inc., Irvine, CA (US)

( * ) Notice: Subject to any disclaimer, the term of this patent is extended or adjusted under 35 U.S.C. 154(b) by 388 days.

(21) Appl. No.: 11/551,385

(22) Filed: Oct. 20, 2006

(65) Prior Publication Data

US 2007/0093494 A1 Apr. 26, 2007

Related U.S. Application Data

(60) Provisional application No. 60/730,548, filed on Oct. 25, 2005.

(51) Int. Cl.
*A61K 31/498* (2006.01)
*C07D 487/04* (2006.01)

(52) U.S. Cl. .................. 514/249; 544/242; 544/278; 544/280; 544/281; 514/247; 514/248

(58) Field of Classification Search .............. 544/224, 544/242, 245, 253, 278, 281
See application file for complete search history.

(56) References Cited

U.S. PATENT DOCUMENTS

| | | | |
|---|---|---|---|
| 3,890,319 | A | 6/1975 | Danielewicz et al. |
| 4,195,085 | A | 3/1980 | Stone |
| 4,861,760 | A | 8/1989 | Mazuel et al. |
| 5,021,410 | A | 6/1991 | Burke |
| 5,856,329 | A | 1/1999 | Wheeler et al. |
| 6,174,524 | B1 | 1/2001 | Bawa et al. |
| 6,194,415 | B1 | 2/2001 | Wheeler et al. |
| 6,248,741 | B1 | 6/2001 | Wheeler et al. |
| 6,316,441 | B1 | 11/2001 | Dean et al. |
| 6,410,045 | B1 | 6/2002 | Shultz et al. |
| 6,441,047 | B2 | 8/2002 | Desantis, Jr. |

FOREIGN PATENT DOCUMENTS

WO 03/088973 10/2003

OTHER PUBLICATIONS

Arici et al., "*A short term study of the additive effect of timolol and brimonidine on intraocular pressure*", Eye, 2002, vol. 16, No. 1, pp. 39-43.
Goni, "*12-week study comparing the fixed combination of brimonidine and timolol with concomitant use of the individual components in patients with glaucoma and ocular hypertension*", European Journal of Ophthalmology, vol. 15, No. 5, 2005, pp. 581-590.
Hommer, A.B., et al., *Efficacy and Safety of Unoprostone, Dorzolamide, and Brimonidine in Adjunctive Therapy to Timolol in Patients with primary open-angle glaucoma and ocular hypertension*, Investigative Ophthalmology & Visual Science, vol. 42, No. 4, Supp. Mar. 15, 2001, p. 554.
Hoyng, P.F., et al., *Pharmacological Therapy of glaucoma*, Drugs, vol. 59, No. 3, Mar. 2000 pp. 411-434.
Jackson, et al. "*Cardiovascular effects of timolol, brimonidine and brimonidine/timolol in combination*", IOVS, 2001:42(4):S418 ABS 2250.
Larsson, "Aqueous humor flow in normal human eyes treated with brimonidine and timolol, alone and in combination", IOVS, 1999, vol. 40, No. 4, pp. S515.
Larsson, L.I., *Aqueous humor flow in normal human eyes treated with brimonidine and timolol, alone and in combination*, Arch Ophthalmol/ vol. 119, Apr. 2001, p. 492-495.
Sall, et al., IOVS, 2001, vol. 42, No. 4, pp. S822, ABS 4412.
Schuman, J.S., *Clinical experience with brimonidine 0.2% and timolol 0.5% in glaucoma and ocular hypertentsion*, Survey of Ophthalmology, Vo. 41, Supp. 1, Nov. 1996, p. s27-s37.
Stewart et al., "*Cardiovascular effects of timolol maleate, brimonidine or brimonidine/timolol maleate in comcomitant therapy*", Acta Ophthalmologica Scandinavia, 2002, 80(3), 277-281.
Stewart, W.C., *Perspectives in the medical treatment of glaucoma*, Current Opinion in Ophthalmology, vol. 10, No. 2, Apr. 1999, pp. 99-108.
Wang, R.F., et al., *Comparison of the ocular hypotensive effect of brimonidine, dorzolamide, latanoprost, or artificial tears added to timolol in glaucomatous monkey eyes*, J. of Glaucoma 9:458-62.
Yuksel et al., "*The short-term effect of adding brimonidine 0.2% to timolol treatment in patients with open-angle glaucoma*", Ophthalmologica, 1999, 213(4), 228-233.

*Primary Examiner*—Golam M Shameem
(74) *Attorney, Agent, or Firm*—Allergan, Inc.; Kevin Forrestal

(57) ABSTRACT

Novel compounds and their uses are disclosed herein.

3 Claims, No Drawings

COMPOUNDS AND THEIR USE RELATED TO COMPOSITIONS FOR TREATING DISEASE

CROSS REFERENCE TO RELATED APPLICATIONS

This application is based on, and claims the benefit of, U.S. Provisional Application No. 60/730,548, filed Oct. 25, 2005, and which is incorporated herein by reference.

DESCRIPTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Disclosed herein is a compound having the structural formula

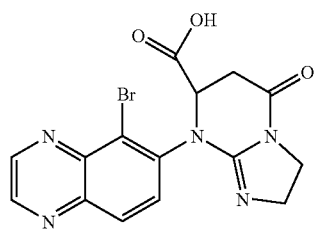

or

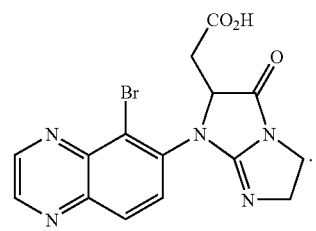

One compound has the structural formula

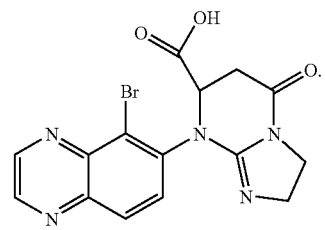

This compound is 8-(5-bromoquinoxalin-6-yl)-5-oxo-2,3,5,6,7,8-hexahydroimidazo[1,2-a]pyrimidine-7-carboxylic acid.

Another compound has the structural formula

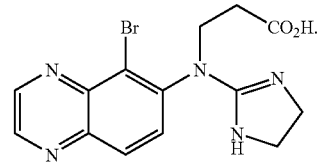

For the purposes of this disclosure, a "compound" includes the compound, pharmaceutically acceptable salts of these compound, tautomers of the compound, or combinations thereof.

Thus, a compound having the structural formula

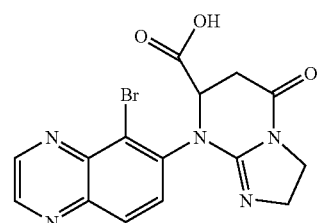

or

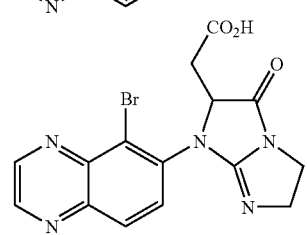

is intended to mean the species depicted by the structural formula, a salt of the species depicted by the structural formula, or a tautomer of the species depicted by the structural formula.

Similarly, if a composition comprises from about 0.0005% to about 0.2% of a compound having the structural formula

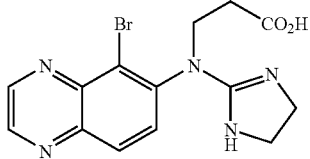

or

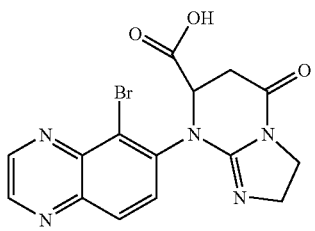

or

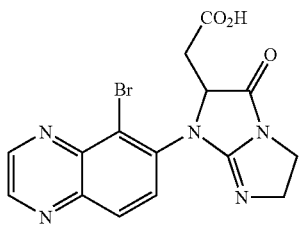

it means that the sum of:
1. the concentration of the species depicted by the structural formula,
2. the total concentration of all pharmaceutically acceptable salts of the species depicted by the structural formula that are present in the composition, and
3. the concentrations of all the tautomers of the species depicted by the structural formula that are present in the composition, is from about 0.0005% to about 0.2%.

Unless otherwise indicated, all concentrations in the claims and description herein given as % are meant to indicate concentration by weight/volume %.

The compound disclosed herein may be prepared by dissolving brimonidine free base in chloroform and adding maleic anhydride. This solution is stirred for about 2 hours. Evaporation of the solvent will yield about 80% pure product, which may be further purified by methods known in the art, such as recrystallization, chromatography, etc.

One embodiment is a composition comprising about 0.5% timolol, from about 0.15% to about 0.2% brimonidine tartrate, and from about 0.0005% to about 0.2% of a compound having the structural formula

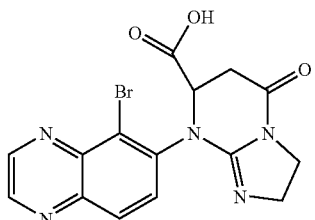

or

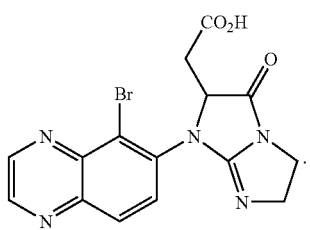

In certain compositions said compound has the structural formula

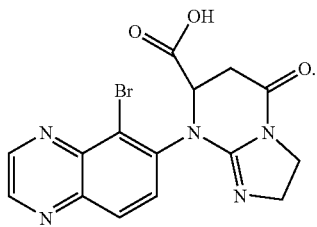

In other compositions said compound has the structural formula

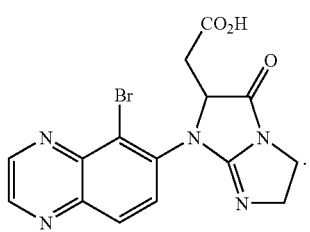

Another composition comprises about 0.5% timolol, from about 0.15% to about 0.2% brimonidine tartrate, and from about 0.0005% to about 0.003% of a compound having the structural formula

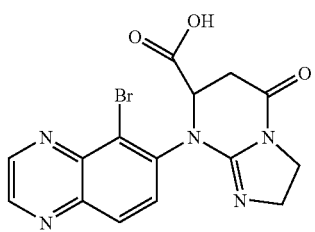

or

-continued

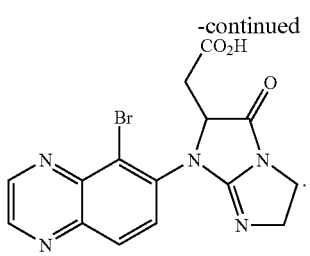

In one composition said compound has the structural formula

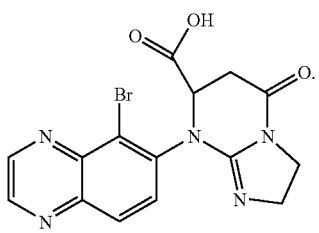

In another composition said compound has the structural formula

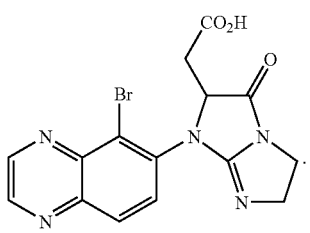

The compositions may be prepared by combining the compound prepared as described above with brimonidine tartrate and timolol in a single composition.

Alternatively, compositions disclosed herein may be prepared by combining the ingredients shown in Table 1 below into a single formulation.

TABLE 1

| Ingredient | Function | Concentration, % (w/v) |
|---|---|---|
| Brimonidine Tartrate | Active | 0.2 |
| Timolol Maleate, EP | Active | 0.68[1] |
| Benzalkonium Chloride, NF, EP | Preservative | 0.005 |
| Sodium Phosphate, monobasic monohydrate, USP | Buffer | 0.43 |
| Sodium Phosphate, dibasic heptahydrate, USP | Buffer | 2.15 |
| Sodium Hydroxide, NF | pH adjust | Adjust pH to 6.9 |
| Hydrochloric Acid, NF | pH adjust | Adjust pH to 6.9 |
| Purified Water, USP, EP | Solvent | q.s. ad |

[1] Equivalent to 0.5% (w/v) Timolol, free base

This composition is then allowed to stand at 25-40° C. for 3-6 months to yield the desired composition. While not wishing to be bound by theory, it is believed that above compound is formed by reaction of brimonidine and maleic acid or maleate ion over time to yield the compound. These compositions are useful for one or more of treating and/or preventing ocular hypertension and/or glaucoma.

While not intending to limit the scope of the invention in anyway, the compounds disclosed herein are useful as standards for determining the purity of a composition prepared having brimonidine and maleic acid and/or maleate salts. Purity may be determined by combining a measured amount of brimonidine with a measured amount of the compound and subjecting the mixture to liquid chromatography, and comparing the peaks to those of brimonidine and the compound analyzed alone. The relative responses of the two compounds to the detection system of the liquid chromatography system is determined by comparing the peak area of brimonidine and the compound to the known amount of each compound added. A response factor K, is obtained by equation 1

$$BA_C/CA_B = K \quad [\text{eq. 1}]$$

where B is the concentration of brimonidine, C is the concentration of the compound, $A_C$ is the area of the compound peak, and $A_B$ is the area of the brimonidine peak.

The sample is then injected into the liquid chromatography system and the ratio of the area of the brimonidine in the sample ($A_B°$) and the compound in the sample ($A_C°$) is used to determine the ratio of the concentration of brimonine (B°) and the concentration of the compound C (C°) in the sample according to equation 2, which uses K from equation 1.

$$B°/C° = KA_B°/A_C° \quad [\text{eq. 2}]$$

The compound disclosed herein can also be used to estimate the age of a composition, stored at ambient temperature, initially comprising brimonidine tartrate and timolol maleate of known amounts and having a pH of 6.9. The age of the compound (λ) in months is determined by equation 3, where B°, T°, and C° are the initial concentrations of brimonidine, timolol maleate, and the compound respectively, in %(w/v).

$$\lambda = C°/(1.1 \times 10^{-3}(B°T°)) \quad [\text{eq. 3}]$$

Equation 3 is an approximation which assumes that B° and T°>>C°. If that is not the case, the age is determined using the rate constant $k=1.1\times10^{-3}$ month$^{-1}$%$^{-1}$ and the appropriate rate expression.

If the composition initially comprises 0.2% brimonidine tartrate and 0.68% timolol maleate. The age of the composition may be determined according to Table 2 below. Alternatively, up to about 36 months, the age is determined by multiplying the concentration of the compound in %(w/v) by 9100.

TABLE 2

| Compound Concentration (% weight/vol) | Age (months) |
|---|---|
| 0.0001 | 1 |
| 0.0002 | 2 |
| 0.0003 | 3 |
| 0.0004 | 4 |
| 0.0006 | 5 |
| 0.0007 | 6 |
| 0.0008 | 7 |
| 0.0009 | 8 |
| 0.001 | 9 |
| 0.0011 | 10 |
| 0.0012 | 11 |
| 0.0013 | 12 |
| 0.0014 | 13 |
| 0.0016 | 14 |
| 0.0017 | 15 |
| 0.0018 | 16 |
| 0.0019 | 17 |
| 0.0020 | 18 |
| 0.0021 | 19 |

TABLE 2-continued

| Compound Concentration (% weight/vol) | Age (months) |
|---|---|
| 0.0022 | 20 |
| 0.0023 | 21 |
| 0.0024 | 22 |
| 0.0026 | 23 |
| 0.0027 | 24 |

Other uses of the compound may include, but are not limited to, chelating agent, buffering agent, pH indicator, cation selection, solubilizing agent, emulsifier, and surfactant. In particular, the compound may be useful as a pH sensitive agent, in for example, making the emulsification and demulsification of a composition pH sensitive, thus giving greater control in the making and breaking of the emulsion. It may also be useful in controlling chelation, such that chelation occurs at a certain pH but the chelated cation is released at another pH, thus providing use in separation.

Brimonidine tartrate is an alpha adrenergic agonist represented by the following formula:

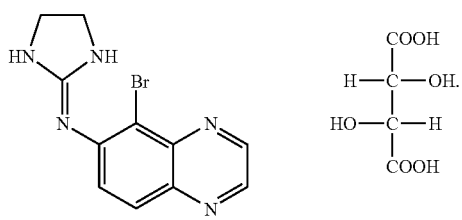

The chemical name for brimonidine tartrate is 5-Bromo-6-(2-imidazolidinylideneamino)quinoxaline L-tartrate.

Timolol maleate is a beta adrenergic agent represented by the following formula:

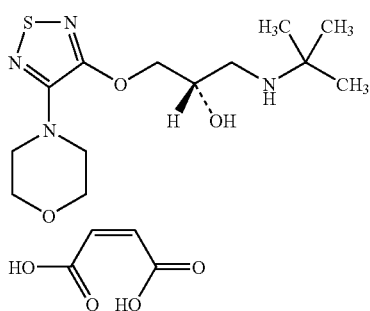

As used herein concentrations of timolol refer to equivalent the concentration of the free base, regardless of any salt that may be used. Timolol maleate is often the salt of choice herein for providing timolol to a composition.

Brimonidine tartrate is available from Allergan, Inc., Irvine, Calif. as an ophthalmic pharmaceutical product having the name Alphagan®.

Timolol is available from various sources, including Merck Co., Rahway, N.J.

The compositions of the present invention are administered topically. The dosage is 0.001 to 1.0, e.g. mg/per eye BID; wherein the cited mass figures represent the sum of the two components, brimonidine and timolol. The compositions of the present invention can be administered as solutions in a suitable ophthalmic vehicle.

In forming compositions for topical administration, mixtures may also be formulated as 0.01 to 0.5 percent by weight brimonidine and 0.1 to 1.0 percent by weight timolol solution in water at a pH of 4.5 to 8.0, e.g. about 6.9, and with about 0.0005% to about 0.2% of a compound having the structural formula:

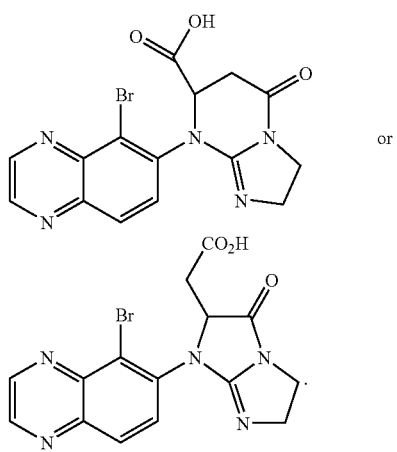

While the precise regimen is left to the discretion of the clinician, it is recommended that the solution be topically applied by placing one drop in each eye two times a day.

Other ingredients in addition to those already mentioned which may be desirable to use in the ophthalmic preparations of the present invention include preservatives, co-solvents and viscosity building agents.

Antimicrobial Preservative:

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. In the prior art ophthalmic products, typically such preservatives are employed at a level of from 0.004% to 0.02%. In the compositions of the present application the preservative, preferably benzalkonium chloride, may be employed at a level of from 0.001% to less than 0.01%, e.g. from 0.001% to 0.008%, preferably about 0.005% by weight. It has been found that a concentration of benzalkonium chloride of 0.005% is sufficient to preserve the compositions of the present invention from microbial attack. This concentration may be advantageously compared to the requirement of 0.01% benzalkonium chloride to preserve timolol in the individual, commercially-available ophthalmic products.

Co-Solvents:

The solubility of the components of the present compositions may be enhanced by a surfactant or other appropriate co-solvent in the composition. Such cosolvents include polysorbate 20, 60, and 80, Pluronic F68, F-84 and P-103, cyclodextrin, or other agents known to those skilled in the art. Typically such co-solvents are employed at a level of from 0.01% to 2% by weight.

Viscosity Agents:

Viscosity increased above that of simple aqueous solutions may be desirable to increase ocular absorption of the active compound, to decrease variability in dispensing the formulation, to decrease physical separation of components of a suspension or emulsion of the formulation and/or to otherwise improve the ophthalmic formulation. Such viscosity building agents include as examples polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art. Such agents are typically employed at a level of from 0.01% to 2% by weight.

The present invention further comprises an article of manufacture comprising packaging material and a pharmaceutical agent contained within said packaging material, wherein the pharmaceutical agent is therapeutically effective for lowering intraocular pressure and wherein the packaging material comprises a label which indicates the pharmaceutical agent can be used for lowering intraocular pressure and wherein said pharmaceutical agent comprises an effective amount of brimonidine and an effective amount of timolol and from about 0.0005% to about 0.2% of a compound having the structural formula:

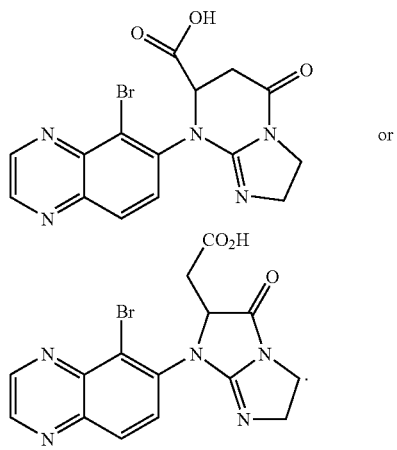

or

EXAMPLE 1

The composition of Table 2 is prepared and stored in containers at ambient temperatures for later dispensing. Nine months later, the composition is administered topically to the eyes of patient for the treatment of glaucoma. Administration is carried out twice a day. A significant reduction in intraocular pressure is observed, and continues while the patient continues to receive the treatment.

EXAMPLE 2

Brimonidine (7.0 g) and maleic anhydride (3.53 g) were added to ethanol free chloroform (200 ml) and heated to 50° C. overnight. The solvent was evaporated and the residue slurried in MeCN (50 ml) at 30° C. for 2 h. The resultant solid was filtered washed with MeCN (25 ml) and dried in an oven at 40° C. to yield 10.5 g of 8-(5-bromoquinoxalin-6-yl)-5-oxo-2,3,5,6,7,8-hexahydroimidazo[1,2-a]pyrimidine-7-carboxylic acid.

What is claimed is:

1. A compound having the structural formula

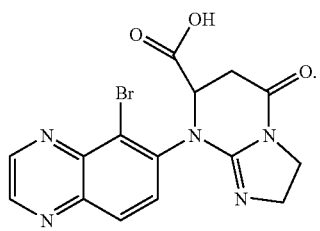

2. A composition comprising about 0.5% timolol, from about 0.15% to about 0.2% brimonidine tartrate, and from about 0.0005% to about 0.2% of a compound having the structural formula

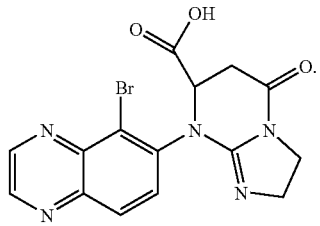

3. A composition comprising about 0.5% timolol, from about 0.15% to about 0.2% brimonidine tartrate, and from about 0.0005% to about 0.003% of a compound having the structural formula

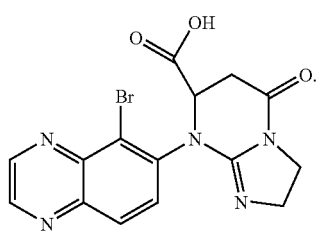

* * * * *